United States Patent
Haghighat-Khansari et al.

(10) Patent No.: US 9,459,193 B2
(45) Date of Patent: Oct. 4, 2016

(54) STENT HOLDER HAVING A REDUCED PROFILE

(71) Applicant: Abbott Cardiovascular Systems Inc., Santa Clara, CA (US)

(72) Inventors: Kiarash Haghighat-Khansari, San Jose, CA (US); David Pinson, Mountian View, CA (US); Marika Kamberi, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 260 days.

(21) Appl. No.: 14/133,321

(22) Filed: Dec. 18, 2013

(65) Prior Publication Data

US 2015/0168270 A1   Jun. 18, 2015

(51) Int. Cl.
*A61F 2/95* (2013.01)
*G01N 13/00* (2006.01)
*G01N 33/15* (2006.01)

(52) U.S. Cl.
CPC .............. *G01N 13/00* (2013.01); *A61F 2/95* (2013.01); *A61F 2250/0067* (2013.01); *B01L 2300/0609* (2013.01); *G01N 33/15* (2013.01); *G01N 2013/006* (2013.01)

(58) Field of Classification Search
CPC ... A61F 2/95; B01L 2300/0609; B01L 99/00
See application file for complete search history.

(56) References Cited

U.S. PATENT DOCUMENTS

| | | | | |
|---|---|---|---|---|
| 2,005,424 A | * | 6/1935 | Kindle | F42B 6/08 473/583 |
| 2,655,128 A | * | 10/1953 | Ransburg | B05B 5/082 118/500 |
| 2,730,988 A | * | 1/1956 | Starkey | B05B 5/082 118/314 |
| 2,930,620 A | * | 3/1960 | Brooks | F42B 6/08 30/337 |
| D236,465 S | * | 8/1975 | Hamilton | 473/583 |
| D290,084 S | * | 6/1987 | Klapperich | D7/688 |
| 4,763,567 A | * | 8/1988 | Dalquist, III | A23L 1/1815 366/247 |
| 5,354,129 A | * | 10/1994 | Yowell | B01F 7/00008 241/282.1 |
| 5,403,090 A | * | 4/1995 | Hofer | B01F 15/00922 366/142 |
| 5,417,493 A | * | 5/1995 | Ericson | B01F 7/00583 366/129 |
| D384,126 S | * | 9/1997 | Graham | D22/107 |
| D400,957 S | * | 11/1998 | Botruff | D22/100 |
| 6,056,993 A | * | 5/2000 | Leidner | A61F 2/06 427/184 |
| D440,476 S | * | 4/2001 | Del Gaone | D8/14 |
| 6,497,157 B1 | * | 12/2002 | Viegas | G01N 13/00 73/863 |

(Continued)

OTHER PUBLICATIONS

Drug Release, General Chapters (724), U.S. Pharmacopeia, 10 pgs.

*Primary Examiner* — David A Rogers
(74) *Attorney, Agent, or Firm* — Squire Patton Boggs (US) LLP (57) ABSTRACT

A stent holder for securely holding a drug eluting stent (DES) during a real-time or an accelerated in-vitro drug release test of a therapeutic substance contained in or on the DES. The holder has a retainer portion and a wire portion separable from the retainer. The holder has a narrowed or reduced profile resulting in less disruptive flow in and around the stent during the accelerated in-vitro drug release test.

20 Claims, 5 Drawing Sheets

(56) References Cited

U.S. PATENT DOCUMENTS

| | | | | |
|---|---|---|---|---|
| 6,565,659 | B1* | 5/2003 | Pacetti | B05C 11/08 118/500 |
| 6,582,116 | B2* | 6/2003 | Nielsen | B01F 7/00033 366/279 |
| 6,743,462 | B1* | 6/2004 | Pacetti | A61L 31/10 427/2.1 |
| 6,863,430 | B2* | 3/2005 | Berube | B01F 13/002 366/129 |
| 6,982,004 | B1* | 1/2006 | Malik | A61F 2/91 118/309 |
| 7,303,329 | B1* | 12/2007 | Flynn | B01F 7/00583 366/129 |
| 7,407,631 | B2* | 8/2008 | Swon | B01F 11/0082 366/273 |
| 8,003,157 | B2 | 8/2011 | Andreacchi et al. | |
| 8,069,814 | B2* | 12/2011 | Guerriero | B05D 1/02 118/500 |
| 8,226,706 | B2* | 7/2012 | Hartley | A61F 2/07 623/1.11 |
| 8,453,598 | B2 | 6/2013 | Plans et al. | |
| D695,872 | S* | 12/2013 | Lennon | D22/115 |
| D701,423 | S* | 3/2014 | Rosser | D7/376 |
| 8,741,379 | B2* | 6/2014 | Van Sciver | B05D 1/02 118/230 |
| 8,815,182 | B2* | 8/2014 | Smit | B01L 3/508 366/273 |
| 2003/0069634 | A1* | 4/2003 | Bialecke | A61L 31/18 623/1.42 |
| 2003/0088304 | A1* | 5/2003 | Rueeger | A61F 2/95 623/1.12 |
| 2004/0013792 | A1* | 1/2004 | Epstein | A61F 2/82 427/2.24 |
| 2004/0062592 | A1* | 4/2004 | Shekalim | A61L 31/10 401/208 |
| 2005/0079274 | A1* | 4/2005 | Palasis | A61L 31/08 427/2.1 |
| 2005/0273161 | A1* | 12/2005 | Malik | A61F 2/91 623/1.42 |
| 2007/0212477 | A1* | 9/2007 | Feng | B05B 3/1014 427/2.1 |
| 2008/0067728 | A1* | 3/2008 | Plans | A61F 2/82 269/47 |
| 2009/0093870 | A1* | 4/2009 | Menendez | B05D 1/02 623/1.11 |
| 2010/0312328 | A1* | 12/2010 | Shulze | A61F 2/90 623/1.16 |
| 2012/0029616 | A1* | 2/2012 | Guerriero | B05D 1/02 623/1.15 |
| 2013/0149432 | A1 | 6/2013 | Chen et al. | |
| 2013/0241133 | A1* | 9/2013 | Plans | A61F 2/82 269/47 |
| 2014/0193569 | A1* | 7/2014 | Huang | A61L 31/08 427/2.25 |
| 2014/0299054 | A1* | 10/2014 | Rego | B05B 15/025 118/502 |
| 2016/0023234 | A1* | 1/2016 | Plans | A61F 2/82 269/47 |

* cited by examiner

STENT HOLDER HAVING A REDUCED PROFILE

FIELD OF THE INVENTION

The present invention relates to implantable medical devices and more particularly medical device holders used during the real-time or accelerated drug-release testing.

BACKGROUND OF THE INVENTION

The localized drug delivery from a drug-eluting stent (DES) has been shown to be quite effective and accepted as one of the most promising treatment methods for preventing restenosis after stenting procedures. For example, a polymeric coating on a DES is designed to sustain appropriate drug release kinetics in order to deliver the therapeutic dose of the drug for the required time interval at the treatment site. An estimation of the real-time release rate is critical for characterization of the DES dosage forms.

With respect to testing drug elution properties of a DES, there are certain challenges to overcome. Most notably, when evaluating the sustained release of a candidate DES structure the test can consume significant time, spanning weeks or months for sustained release of these dosage forms. This is disadvantageous in early research, and therefore not conducive for efficient management of product development. An accelerated (short-term) in-vitro release method is helpful for achieving a more rapid assessment of the formulation and processing variables. Accelerated in-vitro drug release testing is also used as a quality control tool to (i) ensure the consistency of the product performance from batch-to-batch and (ii) assure the stability of the product during the established shelf life.

Characterization of in-vitro drug release profiles for drug products and medical devices with therapeutic agents is routinely accomplished using commercially available automated or semi-automated equipment fitted with specialized holders to accommodate a variety of drug products or devices. Chapter 724 in the US Pharmacopeia (USP) lists several suitable release apparatus designs with the most common applications for each type. The Apparatus 7 (Reciprocating Holder) variety has been used to characterize the release profile of the drug substance used on a coated stent, e.g., Everolimus, when submersed in a release media, e.g., porcine serum. Apparatus 7 utilizes a reciprocating sample holder to dip the drug eluting device in a vessel, e.g., a test tube, containing release media. There are, however, only a limited number of commercially available Apparatus 7 sample holder designs to accommodate a wide variety of drug/device configurations. As a result, companies often design and build custom sample holders to suit specific needs since commercially available choices have limited usefulness.

Figure 1A:
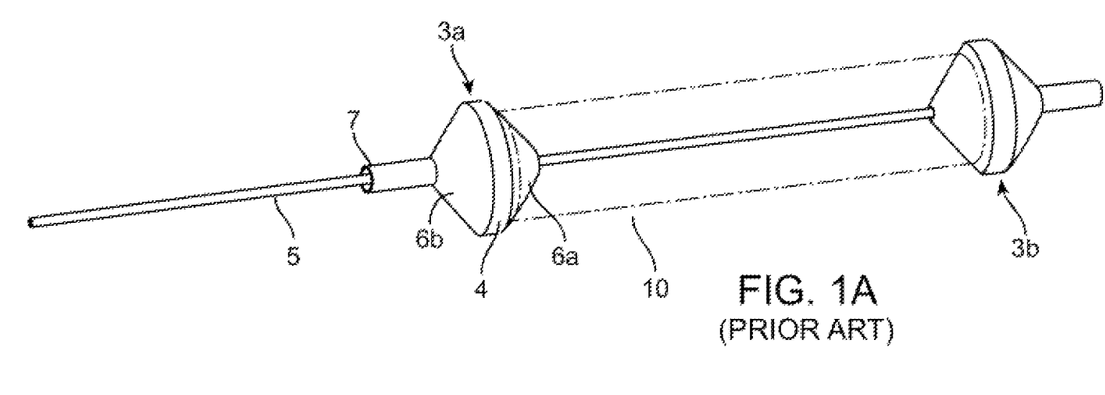
FIG. 1A is a perspective view of a first prior art stent holder.
Figure 1B:
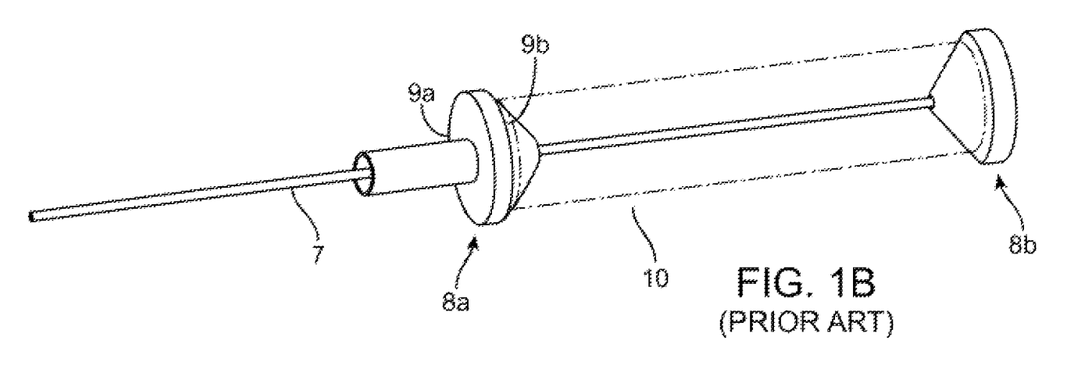
FIG. 1B is a perspective view of a second prior art stent holder.

The most frequently used types of Apparatus 7 sample holder designs for holding a stent during dipping employ a pair of cylindrical or frustoconical bodies received over a mandrel. A pair of collets, at least one of which being capable of sliding along a carrying mandrel, engages each end of the stent. The arrangement secures a stent on the holder while the stent is dipped. FIGS. 1A and 1B illustrate in perspective examples of two such Apparatus 7-type reciprocating holders. Referring to FIG. 1A, the stent holder, shown supporting a stent 10, has two ends 3a, 3b received over a wire 5. Each end 3a, 3b has opposed conical faces 6a, 6b, or frustoconical bodies mated together at their respective frustums with a cylindrical portion 4 separating the frustums. The end 3a is movable along the mandrel 5 while the end 3b is fixed. End 3a has a collar 7. Referring to FIG. 1B, there is a second type of Apparatus 7-type reciprocating holder. It also has a pair of brackets 8a, 8b received over a mandrel. Each bracket has a frustoconical shape 9b arranged to face each other. Stent ends are placed against the conical surface. The sliding end 8a moves towards or away from the other end 8b according to the length of the stent.

The design types in FIGS. 1A and 1B do not, generally speaking, produce an optimal flow profile of release medium over drug-containing surfaces of a medical device during the drug release testing, especially in the case of a stent with both exterior and interior surfaces coated. This conclusion was reached based on, e.g., inconsistencies seen between measured in-vivo vs. in-vitro release properties for the same product. As a result, it was concluded that the known Apparatus 7-type holders tend to cause significant variability in the amount of drug released at each dipping time point, compromising the precision and accuracy of the test. The concern is most serious for stents drug coated on both interior and exterior surfaces.

Accordingly, there is a need to provide a stent or scaffold holder that reduces variability in a drug release profile measured during a real-time or an accelerated in-vitro drug release test of a medical device, such as a stent, where the variability is due to an undesirable flow profile over drug-eluting surfaces of the medical device caused by interfering surfaces of the medical device holder. An improved medical device holder should produce more accurate quality assurance from batch-to-batch of manufactured medical devices; provide better guidance during product development; and/or more accurate predictions of the in-vivo response (when an in vitro/in vivo correlation is established) when using an accelerated in-vitro drug release test method.

SUMMARY OF THE INVENTION

The invention provides a medical device holder that satisfies one or more of these objectives. The holder is capable of securely holding a medical device, preferably a drug-eluting stent (DES), in a vertical alignment for dipping while avoiding the drawbacks of the prior art holders.

The holder includes a narrow cross section or flow profile. In a preferred embodiment there is a triangle-shaped base and triangle-like and movable retainer (sized to receive a DES) that significantly reduces impedance of a free flow of release media to thereby expose interior or hidden surfaces, e.g., side and luminal surfaces or surfaces close to the holder supporting surfaces of a DES, during a real-time or an accelerated drug release test. The resulting free flow of release media to both interior and exterior surfaces will result in more reproducible and reliable drug release profile results.

A preferred holder includes a shouldered design to better assure that a DES remains securely in place while letting release media freely drain off the holder when changing to a next dip interval. This shouldered feature can enhance the accuracy and precision of the drug release determination by minimizing carryover. The holder can also be used with a wide variety of DES sizes, both in length and diameter, as compared to existing holders, without detracting from the desirable low or minimal profile features.

This preferred holder, which may be used with either a drug-eluting stent or scaffold, has two separable parts. The first part is a core wire with one end shaped as an isosceles or equilateral triangle (in two possible base widths of about 8 to 9 mm and about 12 to 13 mm for different outer diameter sizes of stents). The triangle shape (isosceles or equilateral) end of the core wire helps with stable seating of the stent at one end of the holder. The core wire can be in different lengths for different lengths of the stent.

The second part is a metallic retainer, which slides over the core wire and brackets the stent so that the stent is held between the triangular-shaped end of the core wire and the retainer, thereby stabilizing the stent in place. The retainer has a flat surface (in two widths of about 8 to 9 mm and about 12 to 13 mm as needed for different stent diameter sizes). It also has a thin frontal profile of about 2 to 3 mm for both width sizes.

The retainer also has a collar that discourages sliding movement along the wire during dipping yet provides very little increase in frontal profile or surfaces to interfere with the flow of release media or retention of the media when the holder is removed from the test container (thereby avoiding contamination with subsequent testing). Such a collar is sufficient to keep the retainer in its manually-positioned placed during the dipping of the stent and holder in a test container holding the release medium.

There are two profile sizes for the holders, a small profile and a large profile. Either of these holders can come in various total length of core wire to compensate for different lengths of stents/scaffolds. A small profile holder: intended for stent/scaffold with an outer diameter (OD) of about 7 mm and lower (most of coronary stent/scaffold as well as small peripheral stent/scaffold). The base of the triangle-shaped end of the core wire and the width of the retainer are about 8 to 9 mm. The length of the core wire can be in the range of 70 mm to 150 mm (or longer) for different length stents.

Large profile holder: for peripheral stent/scaffold with an outer diameter (OD) of about 8 mm and higher. The base of the triangle-shaped end of the core wire and the width of the retainer are about 12 to 13 mm. The length of the core wire can be in range of 100 mm to 150 mm (or longer) for different length peripheral stents.

In accordance with the foregoing, there is a stent holder, medical device and holder, method of use, method for making, or method for assembly of holder having one or more, or any combination of the following things (1)-(19):

(1) A core wire with one end shaped as an isosceles or equilateral triangle (in two possible base widths of about 8-9 mm or about 12-13 mm for different outer diameter sizes of stent).
(2) The core wire has a diameter of about 0.1 to 5.0 mm.
(3) A member which slides over a core wire. The retainer has flat surfaces (in two widths of about 8-9 mm and about 12-13 mm options for different outer diameter sizes of stents/scaffolds).
(4) The member is a retainer.
(5) The member has a thickness of about 2-3 mm.
(6) The member is made from a single piece of metal or metal alloy.
(7) The member has a width to thickness ratio (W/T) of about 2 to 7, or about 7, 6, 5, 4, 3 or 2.
(8) The member has a front surface that slopes rearward by about 0, 5, 5-10, 20, 10, 30, or about 10-30 degrees.
(9) The member has a rear surface that slopes forward by about 30, 45, 50, 60, or about 40-60 degrees.
(10) Increase in edge roundness front to back for a member.
(11) The member having a collar with a slot.
(12) Any dimension, or combination of the dimensions provided in TABLE 1.
(13) The member has a flat side surface, a width larger than a stent diameter; the member configured to hold the stent, and a thickness that is at least 2 times smaller than the stent diameter.
(14) A stent holder comprising a retainer having a forward end and rear end, the retainer including a collar having a bore and located at the forward end, a forward sloping surface proximal the rear end, a rearward sloping surface proximal the forward end, a maximum width (W) of the stent holder, viewable from a side view of the retainer, a maximum thickness (T) of the stent holder, viewable from a front view of the retainer which is perpendicular to the side view, and wherein the ratio W/T is more than 2.
(15) The apparatus of (14), (17) or (18), or method of (16), in combination with one of, more than one of, or any combination in any order of the following list of things: a holder holding a stent, comprising: a stent disposed between the second end of the wire and the forward sloping surface of the retainer according to the stent holder of (14); further including a mandrel comprising a wire having a first end received in the collar bore and a second end configured to support an end of the stent; wherein the collar includes a slot and the collar forcible receives a wire such that the wire elastically deforms the collar; wherein the retainer is integral with the collar and has a bore aligned with collar bore; wherein the retainer has a flat side surface such that a majority of the thickness of the retainer is T; and/or wherein the mandrel second end comprises the wire shaped into a triangle.
(16) A method for accelerated release testing, comprising the steps of: placing a stent on a stent holder according to (14); dipping the stent and stent holder into a container containing a release medium; removing the stent and holder from the container, and/or dipping the stent and holder into a different container containing a different release medium.
(17) A tubular medical device holder comprising: a wire having a first and second end, the wire extending in a direction perpendicular to a first plane and lying within a second plane; a collet having a bore and the wire first end extends through the bore, the collet further including: sloping surfaces configured to penetrate into a bore of the medical device, a maximum width (W) as measured in the first plane a maximum thickness (T) as measured in the second plane, and the ratio of W/T is about 2 to 7.
(18) An apparatus for holding a medical device, comprising a member having a first and second forwardly sloping surfaces that together form a tip capable of penetrating a bore of the medical device; the first and second forwardly sloping surfaces defining a maximum width (W) of the member, wherein width is measured in a first plane; and in a second plane perpendicular to the first plane the member has a maximum thickness (T); wherein W/T is greater than 2.
(19) The apparatus of (14), (17) or (18), or method of (16), in combination with one of, more than one of, or any combination in any order of the following list of things: wherein W/T is greater than 4 or 5; wherein each of the first and second forwardly sloping surfaces slopes forward by greater than 30, 40 or 50 degrees; further including first and second rearwardly sloping surfaces opposing the first and second forwardly facing surfaces; wherein each of the first and second rearwardly sloping surfaces slopes rearward by greater than 0, 5, 10, and 20 degrees; wherein a forward slope angle for the forwardly sloping surfaces is greater than a rearward slope angle for the rearwardly sloping surfaces; wherein the member defines a bore having a bore axis, the bore configured to receive a wire and the member is symmetric about the bore axis; further including a collar having a slot and defining a bore for forcible receiving a wire such that the wire elastically deforms the collar; and/or wherein the member is integral with the collar and has a bore aligned with collar bore.

INCORPORATION BY REFERENCE

All publications and patent applications mentioned in the present specification are herein incorporated by reference in their entirety, to the same extent as if each individual publication or patent application was specifically and individually indicated to be incorporated by reference in its entirety, including any figures, herein. To the extent there is an inconsistent usage of a word and/or phrase between an incorporated publication or patent application and the present specification, this word and/or phrase will have a meaning consistent with only the manner that the word and/or phrase is used in the present specification.

DETAILED DESCRIPTION OF EMBODIMENTS

For purposes of this disclosure, the following terms and definitions apply:

The term "about" means 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). It is understood that any numerical value, range, or either range endpoint (including, e.g., "about none", "about all", etc.) preceded by the word "about" in this disclosure also describes or discloses the same numerical value, range, or either range endpoint not preceded by the word "about".

Figure 2A:
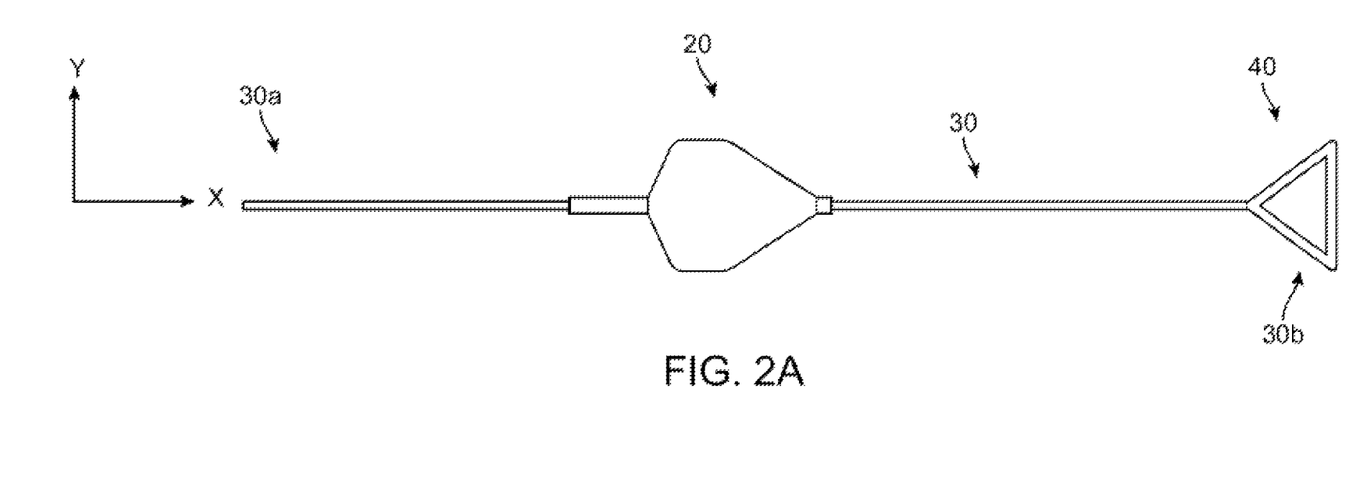
FIGS. 2A and 2B are side and top views, respectively, of a stent holder according to the disclosure. The stent holder includes a first portion and a second portion, which are assembled together in these views. There is also defined an X-Y-Z rectangular coordinate system as a reference for describing aspects of the stent holder. With respect to this reference, the stent holder viewed in the X-Y plane is a side view of the stent holder; the stent holder viewed in the Z-Y plane is a front or rear view of the stent holder; and the stent holder viewed in the X-Z plane is a top or bottom view of the stent holder.
Figure 2B:
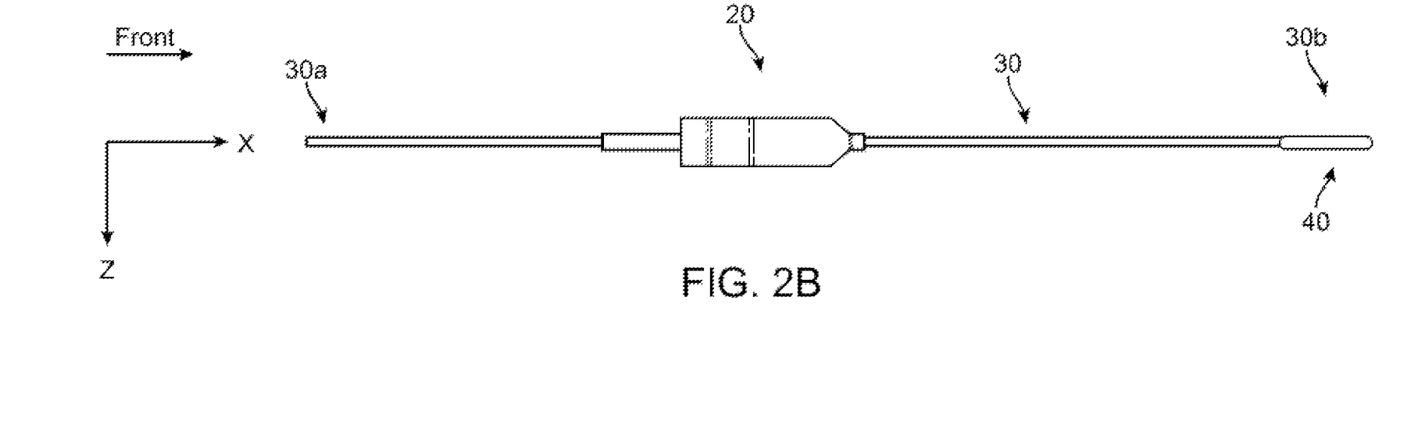
Figure 5:
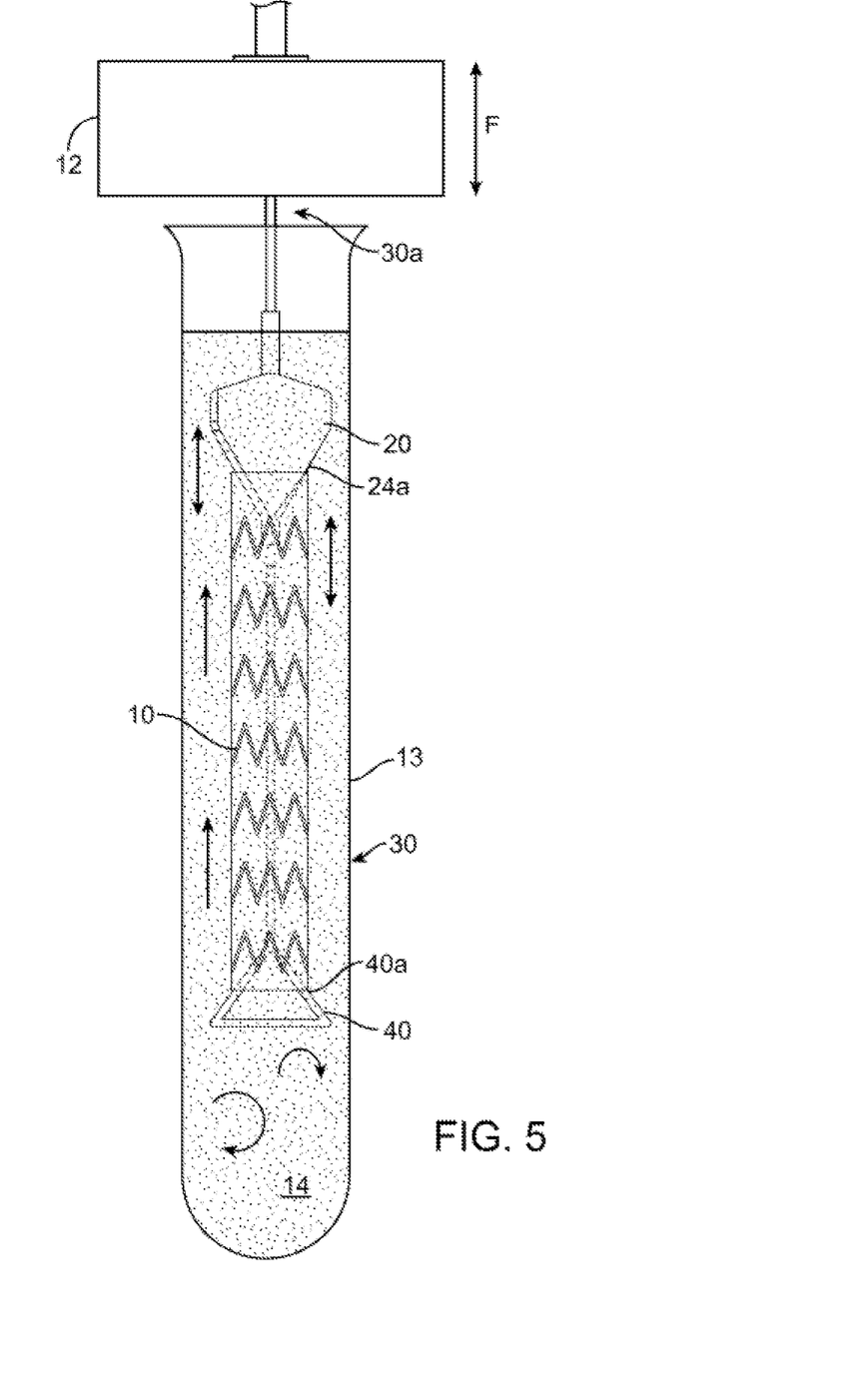
FIG. 5 shows a stent being held by the stent holder of FIGS. 2A-2B during a dipping process in a release medium.

FIGS. 2A-2B show side and top views of a stent holder according to the disclosure. The stent holder includes a retainer 20 separable and capable of being forcibly slid along a mandrel, which in this example is a wire 30. The wire 30 has a first end 30b that receives the retainer 20 and a second end 30b that forms a triangular-shaped base 40. A stent holder is configured for securely holding a stent between the retainer 20 and base 40 during a dipping process for evaluating release rates of a DES. FIG. 5 illustrates such a test. As shown, the stent 10 is held between the base 40 and retainer 20 during a dipping into release medium 14.

Figure 3:
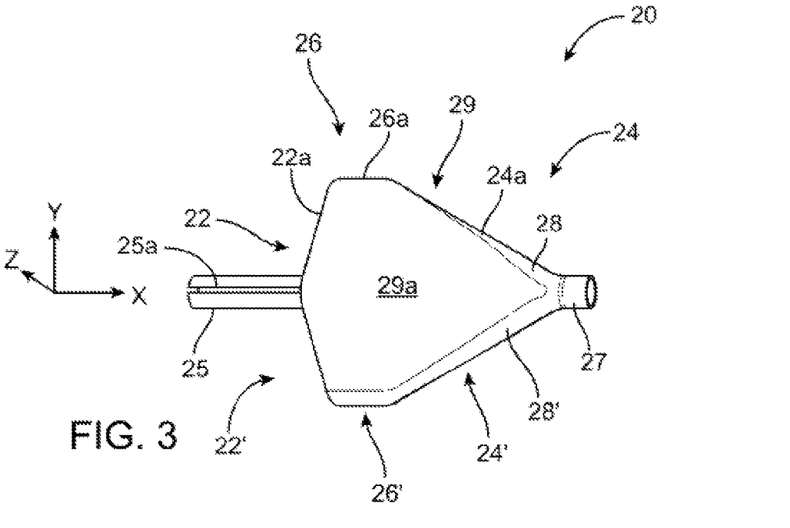
FIG. 3 is a perspective view of a retainer of the stent holder of FIGS. 2A-2B.
Figure 3A:
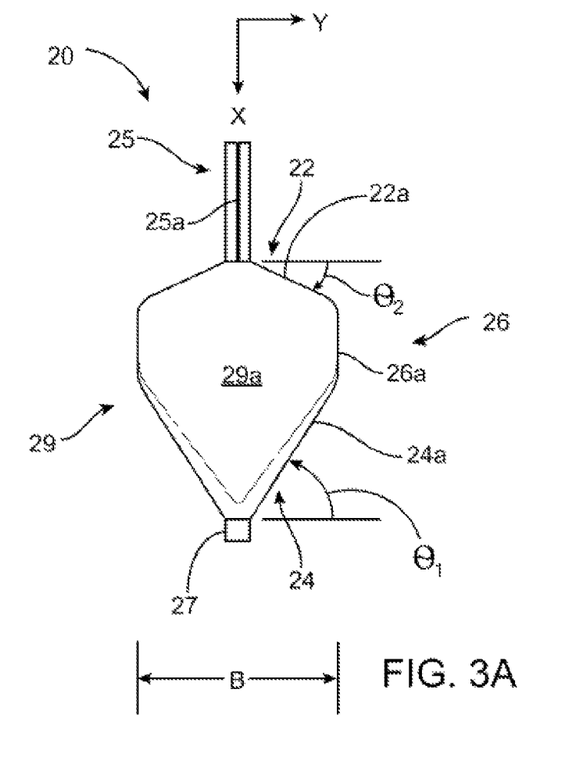
FIGS. 3A and 3B are side and top views, respectively, of the FIG. 3. Retainer.
Figure 3B:
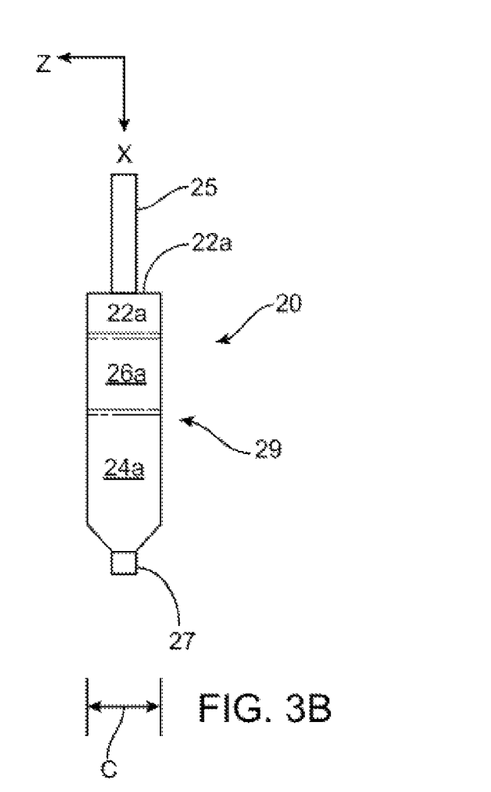

FIGS. 3, 3A and 3B show perspective, side and top views of the retainer 20 from FIGS. 2 and 5, separate from the wire 30. The retainer 20 includes front sides 22 and 22', rear sides 24 and 24' and flat sides 26 and 26'. Together these six sides describe a triangular-like body 29 having a flat side surface 29a. The retainer has a width B and a thickness C which produce an extremely narrow profile in the X-Y plane.

Sides of retainer 20 are distinguished by a rearward slope (side 22 and 22'), forward slope (side 24 and 24') and a relatively flat surface (side 26 and 26'). The retainer 20 is symmetric in the X-Y plane, as seen in FIG. 3A. Thus the top, front and rear side descriptions referred to above have the same features and description, regardless of whether the retainer is viewed from the bottom or top; in other words, it is understood that any description for the sides 22, 26, 24 applies equally to the sides 22', 26', and 24' of the retainer 20.

The retainer 20 forms a rear collar 27 and a front collar 25. The front collar 25 is preferably made significantly longer than rear collar 25 and includes a narrow slot 25a formed in the collar 25 and extending over about the entire length of the collar 25. The collar 25, collar 27 and a bore through the triangular-like body 29 (not shown) of the retainer 20 are aligned with each other so as to provide a circular passage for the wire 30 to pass through the retainer 20 as shown in FIGS. 1A, 1B and 5.

The inner diameter of the collar 25 is slightly less than the inner diameter of the triangular body 29 and rear collar 27. The inner diameter of the collar 25 is also slightly less than the outer diameter of the wire 30. With this configuration for collar 25 and the forming of the slot 25a there is provided a force fit of the retainer 20 onto the wire 30 which retains the retainer 20 in place by friction, essentially between the inner walls of collar 25 and outer surface of the wire 30. As the wire is inserted into the bore of the retainer 20, starting with the collar 27, the wire 30 passes relatively easily until it reaches the collar 25, whereupon the wire end 30a must be forced through the collar 25, resulting in an elastic deflection radially outward of the collar 25 (the slot 25a permits this to happen). Thus, as a result of the elastic deflection radially outward of the collar 25 (caused by forcing the wire 30 through the collar 25 bore) and resulting radial inwardly directed restoring force imposed on the wire 30 surface, there is generated a holding force that prevents the retainer 20 from sliding about on the wire 30 during the dipping process.

Edges that demarcate each of surfaces 22, 22', 24, 24', 26 and 26' from surface 29a are generally rounded; with the degree of roundness increasing from front to back (the front of the retainer 20 is the left-most tip of the collar 25 in FIG. 3). Thus, edges separating surfaces 22 and 22' from surface 29a are more sharp or abrupt (or less rounded) than the edges separating surfaces 26 and 26' from surface 29a. And the edges separating surfaces 24, 24' and 29a are more sharp or abrupt (or less rounded) than the edges separating surfaces 24, 24' from surface 29a.

The portion of the triangular body 29 closest the collar 27 is almost circular, as depicted in FIG. 3. As can be appreciated from the illustrated increase in edge roundness form front to back, this tip of body 29 gradually transitions to a circular shape. This rounded surface is represented by surface 28, 28' which gradually transitions from a relatively sharp edge (nearest surface 26a) to a rounded, almost circular edge adjacent collar 27. In this way the transition, from the flat surface 29a providing the desired small or narrow, and minimally disruptive frontal profile of the retainer 20 to the circular surfaces of the collar 27, is gradual, which tends to cause less disruptive flow in the vicinity of stent portions nearest the surface 26a/28, which engage a stent end. Thus, drug loaded near the stent end will be more exposed to the release medium, which is desirable.

Referring to FIG. 3A, the top side 26 has a surface 26a that lies substantially within the Z-X plane. The surfaces 24 and 22 are oriented in planes rotated at angles θ1 and θ2, respectively, to the Z-Y plane. In other words, the side 22 is sloped rearward by an angle θ2 and the side 24 is sloped forward by an angle θ1 in FIG. 3A. The angle θ1 is about 45, 50, 60, or about 40-60 degrees, and the angle θ2 is about 0, 5, 5-10, 20, 10, 30, or about 10-30 degrees. The angle θ2 may be chosen to be relatively small the requirement is essentially only that release medium easily fall off or away from the holder when removed from the test container, so that residual release medium and eluted drug does not contaminate the test results for a subsequent time point. As for angle θ1 its range can be as low as about 30 degrees. Its purpose is to securely hold the stent yet without damaging the stent when brought into engagement.

Referring to FIGS. 3A and 3B, the maximum thickness of the retainer 20 in the top (or bottom) view is C and the maximum width of the retainer 20 in the side view is B. According to the embodiments, the retainer 20 profile in the Z-Y plane is believed to contribute significantly to the results seen in testing. Thus, it is believed that a critical parameter for the retainer 20 is the ratio of B/C as this characterizes the slimness of the profile of the holder that minimizes interferences between the stent and release medium. The ratio of width to thickness of the retainer, or ratio of B/C can range from about 2 to 7, or about 7, 6, 5, 4, 3 or 2.

In the preferred embodiment retainer 20 is made from a single piece of metal or metal alloy that was milled to the shape shown in FIGS. 3, 3A-3B. Given the dimensions of the bore for receiving the wire, the stent size and durability needed for the piece, it will be appreciated that a thickness of about 2 to 3 mm represents about the smallest dimension possible (given the functional demand on the retainer 20) using a conventional milling machine and material.

Figure 4:
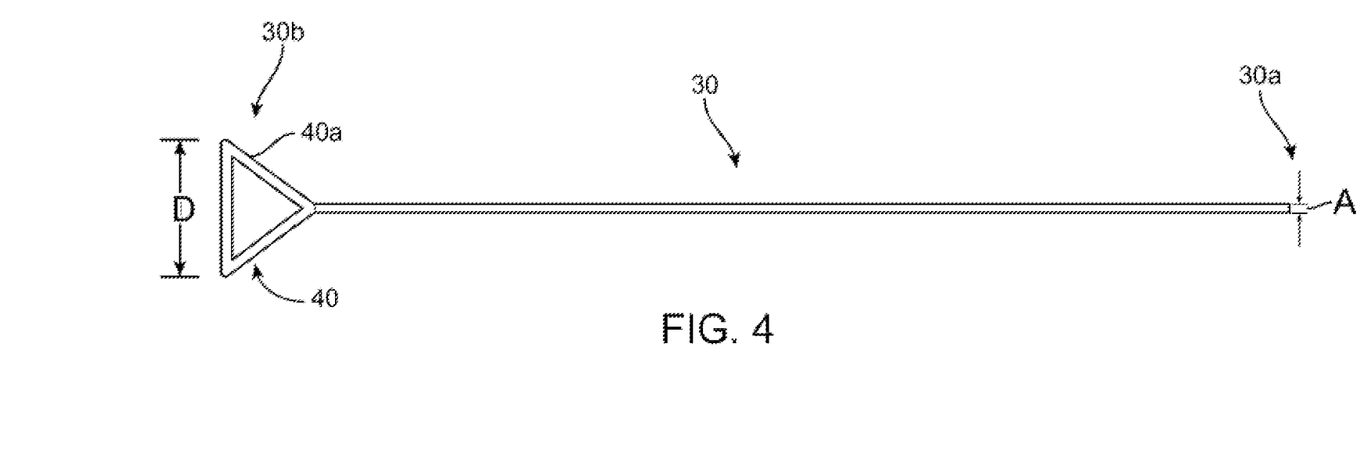
FIG. 4 is a side view of a core wire or wire of the stent holder of FIGS. 2A-2B.

Referring to FIG. 4 there is shown the wire 30 portion of the stent holder. The end 30a of the wire 30 is inserted into the retainer 20. The end 30b forms a triangular-shaped base 40. Like the retainer 20 the base 40 is made narrow, as explained earlier. Also, the base 40 has a minimal amount of surfaces while still providing a base support for holding the end of the stent. The stent end is received on the surfaces 40a so that the tip of the triangle, which may be an isosceles or equilateral type, partially penetrates into the bore of the stent (similarly, the collar 27 and rounded tip of the body 29 penetrates into the stent bore when the stent is held on the stent holder.

With reference to the drawings, TABLE 1, below, summarizes possible ranges of dimensions for a stent holder.

| Dimension | Preferred size (mm) | Range of sizes (mm) |
| --- | --- | --- |
| A | 0.8 | 0.1 to 5.0 |
| B | 9.0 | 0.5 to 20 |
| C | 2.5 | 0.2 to 15 |
| D | 9.0 | 0.5 to 20 |
| Thickness of base 40 | 0.8 | 0.1 to 5.0 |

Referring to FIG. 5 there is shown the stent holder and a stent 10 securely held thereon. The stent holder is being held at end 30a of the wire 30 and shaken within a release medium 14. As can be appreciated more from this view, the small Z-Y plane profile of the holder provided by the retainer and base 20, 40 which hold the stent in place for a holders according to the disclosure causes much less disruption to the flow of release medium in the vicinity of the hidden or interior surfaces of the stent 10.

The first end 30a of the wire is held in an actuator 12 that imparts an oscillating force "F" to the assembly. The actuator 12 causes the stent holder and stent 10 to move about in the release medium 14 of the test tube 13, thereby producing a real-time or an accelerated release of the drug into the release medium. As the holder is moved up and down, the slim profile in the Z-Y plane reduces significantly the interference of the flow over, around, through and into the drug-coated crevices or interior surfaces of the stent during the accelerated test. The ratio of width to thickness for the retainer 20 can be up to 7, greater than 7, or greater than 2, 3, 4, 5, and 6.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. In a stent retaining device having a first retainer and a second retainer, the improvement comprising:
    the first retainer having a forward end and rear end, the first retainer including
        a collar having a bore and located at the forward end,
        a forward sloping surface proximal the rear end,
        a rearward sloping surface proximal the forward end,
        a maximum width (W) of the first retainer, viewable from a side view of the first retainer,
        a maximum thickness (T) of the first retainer, viewable from a front view of first retainer which is perpendicular to the side view, and
        wherein the ratio W/T is more than 2.

2. A stent retaining device of claim 1 holding a stent, the stent retaining device and stent comprising:
    a wire having a first end and a second end comprising the second retainer, the wire being disposed within the bored of the first retainer and a bore of the stent, and
    the stent being disposed between the second end of the wire and the forward sloping surface.

3. The stent retaining device of claim 1, further including a mandrel comprising a wire having a first end received in the collar bore and a second end comprising the second retainer.

4. The stent retaining device of claim 1, wherein the collar includes a slot and the collar forcible receives a wire elastically deforms the collar.

5. The stent retaining device of claim 1, wherein the collar is a first collar and the bore is a first bore, further comprising a second collar having a second bore, the first collar being proximal the forward end and the second collar being proximal the rear end, the first and second collars are integrally formed with the forward and rearward sloping surfaces, and the collars are aligned such that a wire or mandrel can extend through bores of each collar.

6. The stent retaining device of claim 1, wherein the first retainer has opposed first and second flat surfaces everywhere spaced from each other by about the distance T and a widthwise extent of about W.

7. The stent retaining device of claim 1, further including a mandrel comprising a wire having a first end received in the collar bore and a second end comprising the second retainer shaped into a triangle.

8. The stent retaining device of claim 1, wherein the first retainer has first and second flat surfaces, each of which having a perimeter describing the rearward and forward sloping surface and W.

9. The stent retaining device of claim 8, wherein the first retainer includes a first and second collar, wherein both the rearward sloping surface and the forward sloping surface is disposed between the first and second collars.

10. A tubular medical device holder comprising:
   a wire having a first and second end, the wire extending in a direction perpendicular to a first plane and lying within a second plane;
   a collet having a bore and the wire first end extends through the bore, the collet further including:
      sloping surfaces configured to penetrate into a bore of the medical device,
      a maximum width (W) as measured in the first plane
      a maximum thickness (T) as measured in the second plane, and
      the ratio of W/T is about 2 to 7.

11. The tubular medical device holder of claim 10, wherein the collet has first and second flat surfaces, each of which having a perimeter describing the sloping surfaces and W.

12. In an apparatus for holding a medical device between a first member and a second member, the improvement comprising:
   the first member having a first and second forwardly sloping surface that together form a tip capable of penetrating a bore of a medical device;
   the first and second forwardly sloping surfaces defining a maximum width (W) of the first member, wherein width is measured in a first plane; and
   in a second plane perpendicular to the first plane the first member has a maximum thickness (T);
   wherein W/T is greater than 2.

13. The apparatus of claim 12, wherein W/T is greater than 4 or 5.

14. The apparatus of claim 12, wherein each of the first and second forwardly sloping surfaces slopes forward by greater than 30, 40 or 50 degrees and less than 90 degrees.

15. The apparatus of claim 12, further including first and second rearwardly sloping surfaces opposing the first and second forwardly facing surfaces.

16. The apparatus of claim 15, wherein each of the first and second rearwardly sloping surfaces slopes rearward by greater than 0, 5, 10, and 20 degrees.

17. The apparatus of claim 12, wherein a forward slope angle of the forwardly sloping surfaces is greater than a rearward slope angle of the rearwardly sloping surfaces.

18. The apparatus of claim 12, wherein the first member defines a bore having a bore axis, the bore configured to receive a wire and the first member is symmetric about the bore axis.

19. The apparatus of claim 12, the first member further including a collar having a slot and defining a bore for forcible receiving a wire such that the wire elastically deforms the collar.

20. The apparatus of claim 12, wherein the first member includes a first and second collar, wherein the first and second forwardly sloping surfaces are disposed between the first and second collars and the tip comprises one of the first and second collars.

* * * * *